(12) United States Patent
Markel et al.

(10) Patent No.: US 8,197,465 B2
(45) Date of Patent: Jun. 12, 2012

(54) MAGNET CUFF FOR VASCULAR CATHETERS AND BLOODLINES

(75) Inventors: David F. Markel, Collegeville, PA (US); Timothy Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 695 days.

(21) Appl. No.: 11/083,500

(22) Filed: Mar. 18, 2005

(65) Prior Publication Data

US 2005/0222593 A1    Oct. 6, 2005

Related U.S. Application Data

(60) Provisional application No. 60/554,857, filed on Mar. 19, 2004.

(51) Int. Cl.
*A61M 25/098* (2006.01)
*A61N 2/00* (2006.01)

(52) U.S. Cl. .............. 604/529; 600/9; 600/12

(58) Field of Classification Search ........... 600/12; 604/43, 528; 210/222, 223
See application file for complete search history.

(56) References Cited

U.S. PATENT DOCUMENTS

| | | | |
|---|---|---|---|
| 3,358,676 A | 12/1967 | Frei et al. | |
| 3,674,014 A * | 7/1972 | Tillander | 600/434 |
| 4,350,161 A | 9/1982 | Davis, Jr. | |
| 4,468,216 A * | 8/1984 | Muto | 604/43 |
| 4,619,247 A | 10/1986 | Inoue et al. | |
| 4,717,387 A | 1/1988 | Inoue et al. | |
| 5,041,092 A | 8/1991 | Barwick | |
| 5,049,140 A | 9/1991 | Brenner et al. | |
| 5,269,759 A * | 12/1993 | Hernandez et al. | 604/96.01 |
| 5,405,329 A * | 4/1995 | Durand | 604/164.01 |
| 5,431,640 A * | 7/1995 | Gabriel | 604/270 |
| 5,464,023 A * | 11/1995 | Viera | 600/585 |
| 5,540,648 A | 7/1996 | Yoon | |
| 5,542,938 A | 8/1996 | Avellanet et al. | |
| 5,573,518 A | 11/1996 | Haaga | |
| 5,578,003 A | 11/1996 | Borger | |
| 5,630,804 A | 5/1997 | Imada et al. | |
| 5,713,877 A | 2/1998 | Davis | |
| 5,743,843 A | 4/1998 | Berman et al. | |
| 5,772,627 A * | 6/1998 | Acosta et al. | 604/22 |
| 5,813,971 A | 9/1998 | Broderick | |
| 5,931,818 A * | 8/1999 | Werp et al. | 604/270 |
| 5,944,023 A | 8/1999 | Johnson et al. | |
| 6,013,038 A * | 1/2000 | Pflueger | 600/585 |
| 6,030,334 A | 2/2000 | Cox et al. | |
| 6,099,542 A | 8/2000 | Cohn et al. | |

(Continued)

FOREIGN PATENT DOCUMENTS

EP    0370158 A1    5/1990
JP    60-68865 A    4/1985

OTHER PUBLICATIONS

Abstract—Ostomy Wound Manage, 44(5): 24-9,May 1998, Szor et al.

(Continued)

*Primary Examiner* — Corrine M McDermott
*Assistant Examiner* — Melissa Ryckman
(74) *Attorney, Agent, or Firm* — Glenn M. Massina; Fox Rothschild LLP

(57) ABSTRACT

A catheter (100) having a catheter body (102) having a proximal end (106) and a distal end (104) and a proximal portion fixedly connected to the proximal end. A magnet (120,220, 320) is disposed around the catheter body (112) distally of the proximal portion and may be contained within a hub (208, 308).

20 Claims, 4 Drawing Sheets

U.S. PATENT DOCUMENTS

| | | | |
|---|---|---|---|
| 6,159,145 A * | 12/2000 | Satoh | 600/12 |
| 6,168,580 B1 | 1/2001 | Yardley | |
| 6,179,806 B1 | 1/2001 | Sansoucy | |
| 6,524,303 B1 | 2/2003 | Garibaldi | |
| 6,589,159 B2 | 7/2003 | Paturu | |
| 6,656,199 B1 | 12/2003 | Lafontaine | |
| 7,137,976 B2 | 11/2006 | Ritter et al. | |
| 7,211,082 B2 | 5/2007 | Hall et al. | |
| 7,249,604 B1 | 7/2007 | Mohanraj | |
| 2002/0198435 A1 | 12/2002 | Paturu | |
| 2003/0187320 A1 | 10/2003 | Freyman | |

OTHER PUBLICATIONS

Listing of Prior Art articles (one sheet) entitled "Blood dynamics", (source and date unknown).

Article—"Magnetic Wound Treatment Externally Applied Magnetic Fields", 3 pages, from website data Feb. 10, 2005, http://www.biomagnetic.org/wound % 20 treatment%20 research.html.

International Search Report dated Sep. 24, 2007; PCT/US05/08939 (4) pages.

Written opinion dated Sep. 24, 2007; PCT/US05/08939 (5) pages.

Supplementary European Search Report dated Apr. 20, 2009 EP 05728309 (2 pages).

Supplemental Opinion of European Patent Office in connection with EP05728309.5.

Office Action dated Aug. 3, 2010; Japanese Patent Application No. 2007-504117 (7 pages including translation).

Brunner, "Muscles and Magnets—Can they positively recharge your recuperation", Muscle & Fitness Magazine, May 1997, 68-72.

* cited by examiner

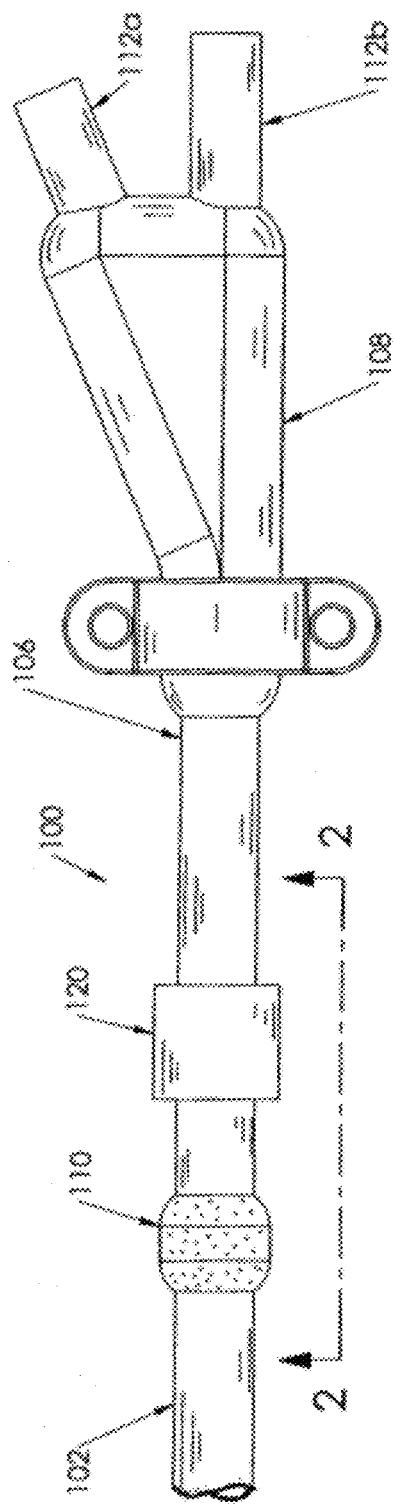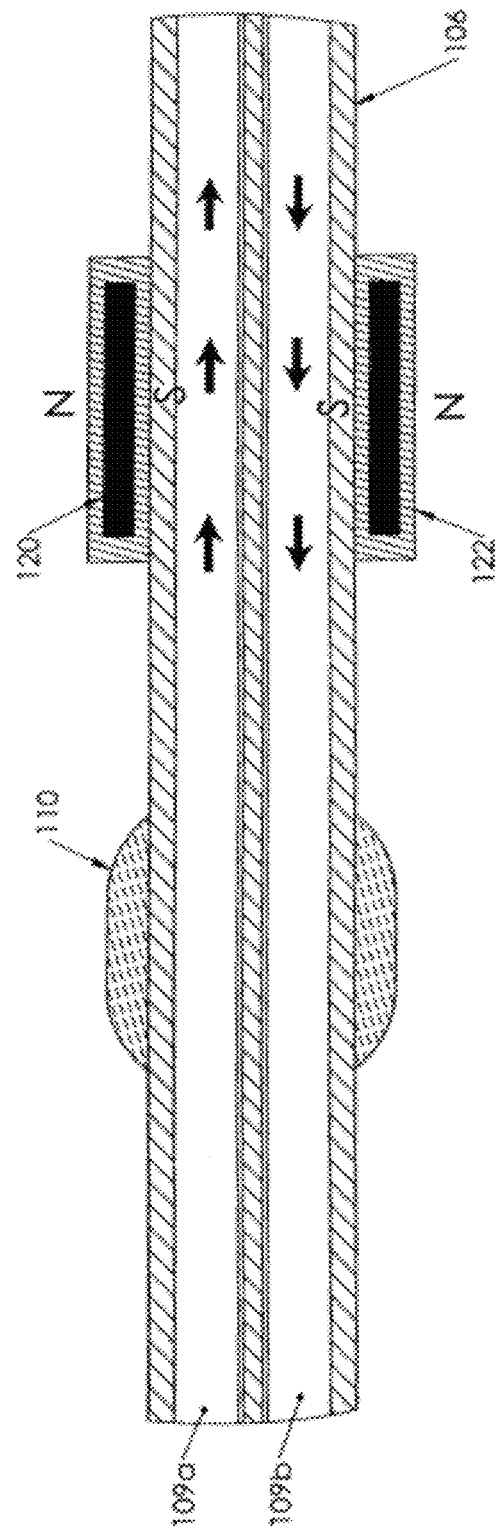

US 8,197,465 B2

MAGNET CUFF FOR VASCULAR CATHETERS AND BLOODLINES

CROSS-REFERENCE TO RELATED APPLICATION

The present application claims the benefit of U.S. Provisional Patent Application Ser. No. 60/554,857 filed on Mar. 19, 2004.

FIELD OF THE INVENTION

The present invention relates to hemodialysis catheters that incorporate a relatively low strength magnet to exert a magnetic field against the blood flowing through the catheter.

BACKGROUND OF THE INVENTION

Catheters are used to provide hemodialysis to patients whose kidneys are no longer able to remove toxins from the blood. The catheter is inserted into a large vein, such as the internal jugular vein, with a portion of the catheter extending externally of the patient. Insertion of the catheter into the vein requires percutaneous incisions in order to access the vein. The trauma incurred by these incisions may result in complications, such as infection, bleeding and slow healing.

Additionally, blood flow through the catheter during hemodialysis is critical to proper treatment and cleansing of the toxins from the blood. Poor blood flow through the catheter results in less efficient dialysis of the blood.

Magnets have been used for centuries to treat various ailments as an alternative to medicinal and drug therapy. Although magnets have not been medically proven to heal the sick and injured, their reputation as a therapeutic device is widely known and accepted.

It is believed that magnets affect the iron and other ionic compounds, such as compounds containing sodium, potassium, and magnesium, in each blood cell, polarizing the blood cells, and attracting the blood cells to the induced magnetic field. The increased blood flow also increases oxygen flow to the wound or damaged area served by the magnetic field, which accelerates the healing process. See Szor, J. K. et al., *Use of Magnetic Therapy to Heal an Abdominal Wound*, Ostomy Wound Manage, 44(5):24-9, 1998 May.

It is also believed that magnets help in the prevention and/or reduction in thrombus formation. Virchow's Triad states that a thrombus formation depends on the viscosity of the blood, injury to the vessel wall and the velocity of the blood flow. It is believed that the application of a magnetic force negates at least two legs of the triangle to increase blood flow. By utilizing the iron content in the red corpuscles, in connection with the repelling force of the south pole, the velocity of the blood is increased through the catheter and into the target vessel. Additionally, utilizing the theory proposed by Szor et al., the magnet will promote faster healing of vessel trauma, thereby effecting the clotting cascade present during vessel injury. Suspension of this thrombus forming mechanism reduces the change of the thrombus, thereby increasing flow through the vessel.

It would be beneficial to provide a magnet attached to a catheter to provide a polarizing effect on blood in the catheter. It is believed that such a device will promote healing of the incision where the catheter is inserted into the patient, as well as increase blood flow through the catheter during dialysis.

BRIEF SUMMARY OF THE PRESENT INVENTION

Briefly, the present invention provides a catheter comprising a catheter body having a proximal end and a distal end and a proximal portion fixedly connected to the proximal end. A magnet is disposed around the catheter body distally of the proximal portion.

Further, the present invention also provides a catheter comprising a catheter body having a proximal end and a distal end and a hub connecting the proximal end and the distal end. A magnet is disposed within the hub.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is a top plan view of a portion of a catheter incorporating an external magnet according to a first embodiment of the present invention.

FIG. 2 is an enlarged sectional view of the catheter and magnet of FIG. 1, taken along line 2-2.

DETAILED DESCRIPTION OF THE INVENTION

Figure 3:
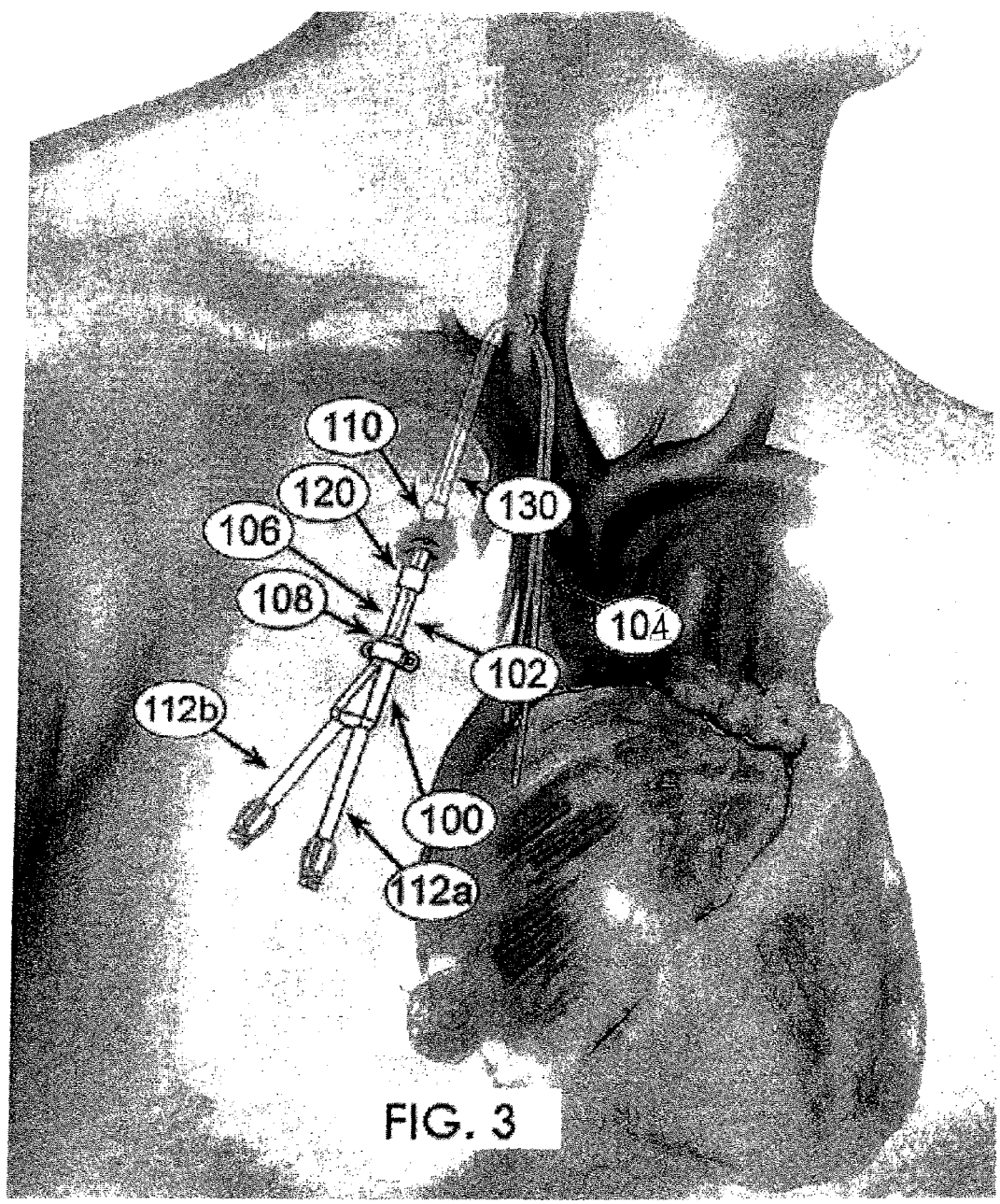
FIG. 3 is a diagram of a catheter according to the first embodiment of the present invention implanted into a patient.

In the drawings, like numerals indicate like elements throughout. Certain terminology is used herein for convenience only and is not to be taken as a limitation on the present invention. The words "proximal" and "distal" refer to the right side and the left side of the catheter with external magnet according to the present invention as shown in FIG. 1. The terminology includes the words above specifically mentioned, derivatives thereof, and words of similar import. The following describes a preferred embodiment of the invention. However, it should be understood based on this disclosure, that the invention is not limited by the preferred embodiment described herein.

Referring to FIGS. 1 and 2, a catheter 100 with an external permanent magnet 120 is shown. The catheter 100 includes a body 102 having a distal end 104 (see FIG. 3), which is intended to be inserted subcutaneously within a patient's blood vessel, and a proximal end 106, which is intended to remain exterior of the patient's body. The proximal end 106 is typically connected to a hub 108, although those skilled in the art will recognize that a hub 108 is not absolutely necessary to enable the present invention. For example, for a single lumen catheter, such as the TESIO® catheter sold by Medical Components, Inc. of Harleysville, Pa., the distal end of the catheter body is connected directly to an extension tube fitting, omitting a hub entirely.

The catheter body 102 may house either a single lumen or a plurality of lumens, as known by those skilled in the art. A single lumen catheter is typically used to either remove fluid from or administer fluid to a patient, while a catheter having a plurality of lumens is typically used to both remove fluid and administer fluid to the patient, often simultaneously, such as during hemodialysis. The catheter 100 shown in FIGS. 1 and 2 is a dual lumen side-by-side catheter, such as the SPLIT-CATH® catheter also sold by Medical Components, Inc. of Harleysville, Pa. A first lumen 109a may be used to withdraw fluid from a patient, while a second lumen 109b may be used to return fluid to the patient. The hub 108 connects the first lumen 109a with a first extension tube 112a and the second lumen 109b with a second extension tube 112b.

A catheter ingrowth cuff 110 is disposed about the exterior of the body 102, distal from the hub 108. Preferably, the cuff 110 is approximately 2 inches (5 centimeters) from the hub 108, although those skilled in the art will recognize that the cuff 110 may be disposed more or less than 2 inches from the hub 108.

The magnet 120 is slidably disposed about the body 102 between the cuff 110 and the hub 108. Preferably, the magnet 120 is constructed from a permanently magnetic material, such as iron, cobalt, nickel, samarium, neodymium, dysprosium, gadolinium, or some other suitable magnetic material, and has a magnetic strength of approximately between 700 and 1,000 Gauss. As shown in FIG. 2, the magnet 120 is preferably encased in a casing 122 constructed from a suitable material, such as a polymer or a rubber, to provide sterility.

For a catheter without a hub, such as the TESIO® catheter as discussed above, the magnet 120 may be disposed between the cuff 110 and an extension tube fitting (not shown). Further, for a catheter without the cuff 110, the magnet 120 is disposed about the catheter body 102 proximate to the hub 108 and spaced substantially from the distal end 104 of the catheter (FIG. 3), between the hub 108 and the entrance site of the catheter 100 into the patient, all as is seen in FIG. 3.

As shown in FIG. 2, the south pole of the magnet 120 is disposed facing or proximate to the body 102, while the north pole of the magnet 120 is disposed distal from the body 102, or facing away therefrom. However, those skilled in the art will recognize that the polarity of the magnet 120 with respect to the body 102 may be reversed without departing from the scope of the present invention.

The magnet 120 may be annularly shaped or the magnet 120 may be comprised of a plurality of magnets dispersed about an annularly shaped casing 122. However, it is important to the inventive aspect of the present invention that the same polarity (north or south) is disposed proximate to the body 102 of the catheter 100.

The catheter 100 is inserted into the patient according to accepted practices, preferably subcutaneously tunneled under the patient's skin, with the cuff 110 disposed within a subcutaneous tunnel 130, as shown in FIG. 3. The magnet 120 is exterior of the tunnel 130 proximate to the entrance of the catheter body 102 into the tunnel 130. It is believed by the inventors that the proximity of the magnet 120 to the tunnel entrance will accelerate healing of the incision that forms the tunnel entrance.

While FIG. 3 shows the catheter 100 having been subcutaneously tunneled, those skilled in the art will recognize that the tunnel may be omitted, with the magnet 120 being located proximate to the incision where the catheter body 102 enters the patient, thereby accelerating healing of the entrance incision.

For use of the catheter 100 in hemodialysis, where blood is being withdrawn and then returned to the patient, the inventors believe that the constant polarity of the magnet 120 proximate to the body 102 may repel the iron ions in the blood and increase the velocity of the blood as the blood travels through the catheter 100, reducing the likelihood of thrombus formation in the catheter 100.

It is also believed that, with the magnet 120 disposed proximate to the insertion site of the catheter 100 into the patient, due to the magnetic force of the magnet 120, blood cells in the patient's bloodstream proximate to the incision site are drawn toward the magnet 120 due to the magnetic attraction of the iron in the blood toward the magnet 120. It is believed that such magnetic attraction also increases blood flow and oxygenation to the incision site, accelerating the healing process.

Figure 4:
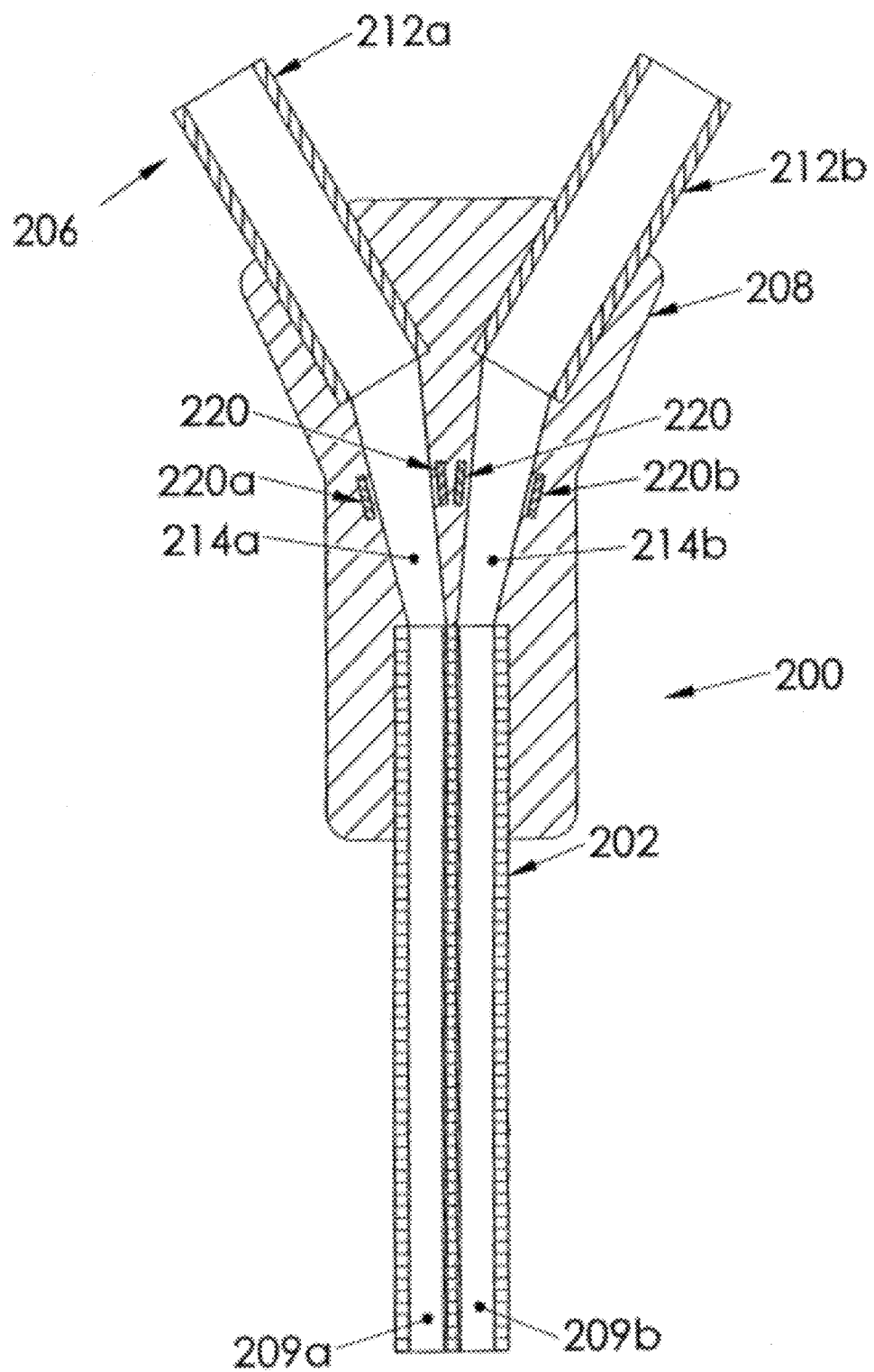
FIG. 4 is a sectional view of a catheter incorporating a magnet in the catheter hub according to a second embodiment of the present invention.

An alternative embodiment of a catheter 200 according to the present invention is shown in FIG. 4. The catheter 200 includes a body 202 having a distal end (not seen), which is intended to be inserted subcutaneously within a patient's blood vessel, and a proximal end 206, which is intended to remain exterior of the patient's body. The proximal end 206 includes a hub 208, which connects the distal end and the proximal end 206.

The catheter 200 shown in FIG. 4 includes first and second lumens 209a, 209b, respectively, that extend distally from the hub 208. The first lumen 209a is used to draw blood from the patient, while the second lumen 209b is used to return blood to the patient after the blood has been treated. Although only first and second lumens 209a, 209b are shown, those skilled in the art will recognize that more or less than two lumens may be used. The hub 208 is used to fluidly connect the first lumen 209a with a first extension tube 212a and to connect the second lumen 209b with a second extension tube 212a. A first fluid passage 214a within the hub 208 fluidly connects the first lumen 209a with the first extension tube 212a, while a second passage 214b within the hub 208 fluidly connects the second lumen 209b with the second extension tube 212b.

A magnet 220 is disposed within the hub 208 so as not to be visible to the patient, and so that the magnet 220 is not seen as an extraneous device on the catheter 200. As can be see from FIG. 4, the magnet 220 includes a first magnet 220a that surrounds at least a portion of the first passage 214a and a second magnet 220b that surrounds at least a portion of the second passage 214b.

Preferably, each of the magnets 220a, 220b are annularly shaped and are each constructed from a permanently magnetic material, such as iron, cobalt, nickel, samarium, neodymium, dysprosium, gadolinium, or some other suitable magnetic material. Also preferably, each magnet 220a, 220b has a magnetic strength of approximately between 700 and 1,000 Gauss. While each magnet 220a, 220b may be a singular annularly shaped magnet, the magnets 220a, 220b may be comprised of a plurality of magnets dispersed along each respective passage 214a, 214b. However, it is important to the inventive aspect of the present invention that the same polarity (north or south) is disposed proximate to its respective passage 214a, 214b.

Figure 5:
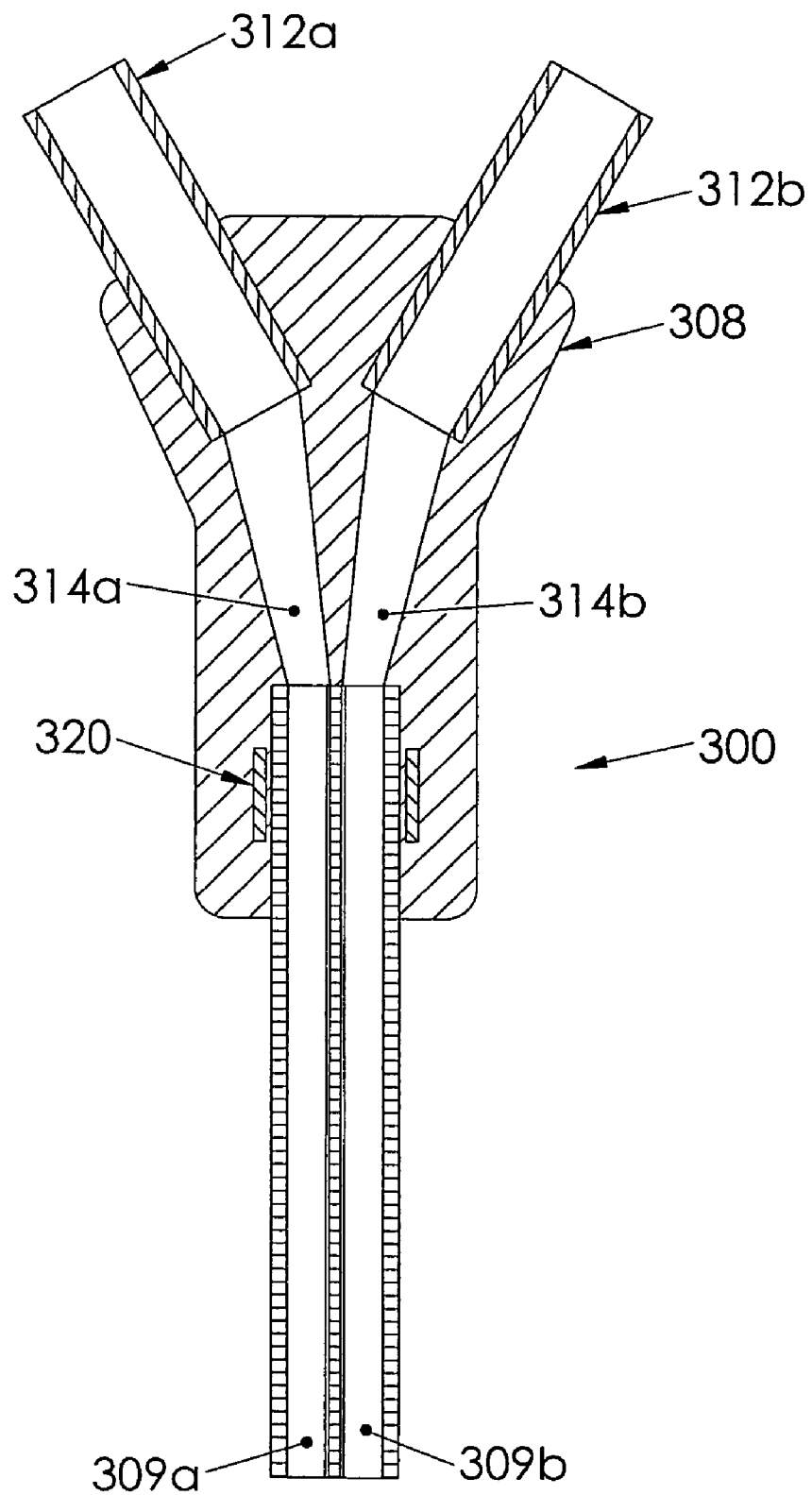
FIG. 5 is a sectional view of a catheter incorporating a magnet in the catheter hub according to a third embodiment of the present invention.

Alternatively, as shown in FIG. 5, an alternate embodiment of a catheter 300 according to the present invention is shown. Instead of utilizing two magnets in the hub as is shown in the catheter 200 described above, the catheter 300 includes a hub 308 with a single annular magnet 320 surrounding proximal ends of catheter lumens 309a, 309b as the lumens 309a, 309b enter the hub 308. The hub 308 serves as a junction for the lumens 309a, 309b to fluidly connect to extension tubes 312a, 312b via passages 314a, 314b formed in the hub 308. While two lumens 309a, 309b are shown, those skilled in the art will recognize that more than two lumens 309a, 309b may be used, and that the magnet 320 will surround all of the lumens within the hub 308.

Preferably, the magnet 320 is annularly shaped and is constructed from a permanently magnetic material, such as iron, cobalt, nickel, samarium, neodymium, dysprosium, gadolinium, or some other suitable magnetic material. Also preferably, the magnet 320 has a magnetic strength of approximately between 700 and 1,000 Gauss. While the magnet 320 may be a singular annularly shaped magnet, the magnet 320 may be comprised of a plurality of magnets dispersed along the distal end of the lumens 309a, 309b. However, it is important to the inventive aspect of the present invention that the same polarity (north or south) is disposed proximate to the lumens 309a, 309b.

The catheters 200, 300 are inserted into the patient in the same manner as the catheter 100 as described above.

While the present invention is described as being used with catheters, those skilled in the art will recognize that the magnets disclosed herein may also be used around other bloodlines in order to improve blood flow through the lines. Such bloodlines may include, but are not limited to, hemodialysis machine bloodlines or any other suitable bloodlines.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A catheter for use in transmission of blood with respect to the vasculature of a patient, comprising:
    a multi-lumen catheter body having a proximal end and an implantable distal portion extending to a distal end, and defining at least two lumen extending therebetween, each lumen having a distal tip opening and a proximal opening for transmission of blood thereinto and out thereof in at least one direction with respect to the vasculature of the patient;
    an in-growth cuff fixedly connected to the catheter body between the proximal and distal ends; and
    a magnet disposed around and external to the catheter body distally of the proximal end and proximal of the in-growth cuff, the magnet having only one of a north pole and a south pole of the magnet disposed facing the catheter body.

2. The catheter according to claim 1, wherein the magnet is annularly shaped to surround an at least one lumen.

3. The catheter according to claim 1, wherein only the south pole of the magnet is disposed facing the catheter body.

4. The catheter according to claim 1, wherein the proximal end includes a hub.

5. The catheter according to claim 1, wherein the magnet is slidably disposed along the body between the cuff and the proximal portion.

6. The catheter according to claim 1, wherein the magnet has a magnetic strength of between 700 and 1000 Gauss.

7. The catheter according to claim 1, wherein the magnet is encased in an annular casing.

8. The catheter according to claim 1, further comprising a hub connecting the proximal end and the distal end.

9. The bloodline according to claim 1, wherein the magnet is a permanent magnet.

10. A catheter assembly for use in transmission of blood with respect to the vasculature of a patient, comprising:
    a multi-lumen catheter body having a proximal end and a distal end, and defining at least two lumen extending therebetween, each lumen having a distal tip opening and a proximal opening for transmission of blood thereinto and out thereof in at least one direction with respect to the vasculature of the patient;
    a proximal portion including a passageway in fluid communication with each lumen of the catheter body;
    a hub connecting the proximal portion and the catheter body and providing fluid communication between each passageway and an associated lumen of the catheter body to establish a respective fluid channel extending between the proximal portion and the distal catheter end; and
    a magnet disposed within the hub and surrounding at least one fluid channel.

11. The catheter assembly according to claim 10, wherein the magnet is a permanent magnet.

12. The catheter assembly according to claim 10, wherein the catheter assembly comprises a plurality of fluid channels.

13. The catheter assembly according to claim 12, wherein the magnet comprises a like plurality of magnets, wherein each of the plurality of magnets is annularly disposed around a respective each of the plurality of fluid channels.

14. The catheter assembly according to claim 13, wherein each of the plurality of magnets has a magnetic strength of between 700 and 1000 Gauss.

15. The catheter assembly according to claim 13, wherein only one of a north pole and a south pole of each of the plurality of magnets is disposed facing each of the respective plurality of lumens.

16. The catheter assembly according to claim 15, wherein only the south pole of each of the plurality of magnets is disposed facing each of the respective plurality of lumens.

17. A flexible medical tubing for transmission of blood at least to a patient, comprising:
    a tubing body having a proximal end and an implantable distal portion extending to a distal end, and defining at least one lumen extending therebetween, each at least one lumen having a distal opening and a proximal opening for transmission of blood thereinto and out thereof in at least one direction with respect to the vasculature of the patient;
    and
    a magnet disposed around and external to the tubing body distally of the proximal portion and proximal of the distal portion, the magnet having only one of a north pole and a south pole of the magnet disposed facing the tubular body, and slidable along the tubing body with the facing pole in direct contact with an annular external surface of the tubing body.

18. The catheter according to claim 1, wherein the magnet is disposed spaced substantially from the distal end of the catheter body.

19. The catheter according to claim 17, wherein the magnet is disposed spaced substantially from the distal end of the tubing body.

20. The catheter according to claim 17, wherein the magnet is a permanent magnet.

* * * * *

UNITED STATES PATENT AND TRADEMARK OFFICE
CERTIFICATE OF CORRECTION

| | | |
|---|---|---|
| PATENT NO. | : 8,197,465 B2 | Page 1 of 1 |
| APPLICATION NO. | : 11/083500 | |
| DATED | : June 12, 2012 | |
| INVENTOR(S) | : Markel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 974 days.

Signed and Sealed this
Second Day of September, 2014

Michelle K. Lee
*Deputy Director of the United States Patent and Trademark Office*